United States Patent [19]

Fukui et al.

[11] Patent Number: 4,533,488

[45] Date of Patent: Aug. 6, 1985

[54] PYRIMIDINE DERIVATIVES

[75] Inventors: Masahiro Fukui; Kisei Kitano; Masami Tanaka; Yasuyuki Goto, all of Yokohamashi, Japan

[73] Assignee: Chisso Corporation, Osaka, Japan

[21] Appl. No.: 525,881

[22] Filed: Aug. 24, 1983

[30] Foreign Application Priority Data

Aug. 26, 1982 [JP] Japan .................. 57-148283

[51] Int. Cl.³ .................. C09K 3/34; G02F 1/13; C07D 239/26; C07D 239/24
[52] U.S. Cl. .................. 252/299.61; 252/299.5; 350/350 R; 544/242; 544/298; 544/335
[58] Field of Search .................. 252/299.61, 299.5; 350/350 R; 544/242, 298, 335

[56] References Cited

U.S. PATENT DOCUMENTS

| | | | |
|---|---|---|---|
| 3,997,536 | 12/1976 | Boller et al. | 252/299.61 |
| 4,062,798 | 12/1977 | Boller et al. | 252/299.61 |
| 4,154,697 | 5/1979 | Eidenschink et al. | 252/299.63 |
| 4,273,929 | 6/1981 | Boller et al. | 252/299.61 |
| 4,311,610 | 1/1982 | Zaschke et al. | 252/299.61 |
| 4,325,830 | 4/1982 | Sethofer | 252/299.61 |
| 4,330,426 | 5/1982 | Eidenschink et al. | 252/299.63 |
| 4,331,552 | 5/1982 | Eidenschink et al. | 252/299.63 |
| 4,348,298 | 9/1982 | Zaschke et al. | 252/299.61 |
| 4,402,849 | 9/1983 | Krauss et al. | 252/299.61 |
| 4,462,923 | 7/1984 | Boller et al. | 252/299.61 |

FOREIGN PATENT DOCUMENTS

| | | | |
|---|---|---|---|
| 2257588 | 6/1973 | Fed. Rep. of Germany | 252/299.61 |
| 54-11887 | 1/1979 | Japan | 252/299.61 |
| 54-41285 | 2/1979 | Japan | 252/299.61 |
| 54-43189 | 4/1979 | Japan | 252/299.61 |
| 55-152777 | 11/1980 | Japan | 252/299.61 |
| 2092169 | 8/1982 | United Kingdom | 252/299.61 |

OTHER PUBLICATIONS

Demus, D., et al., Flüssige Kristalle in Tabellen, VEB Deutscher Verlag für. Grundstoff Industrie, Leipzig, pp. 260–263, (1976).

*Primary Examiner*—Teddy S. Gron
*Attorney, Agent, or Firm*—Fred Philpitt

[57] ABSTRACT

Novel organic compounds useful as a component of liquid crystal compositions are provided which compounds are 5-substituted-2-(4'-substituted biphenylyl)-pyrimidines and 5-substituted-2-[4'-(trans-4''-substituted cyclohexyl) phenyl]pyrimidines expressed by the general formula

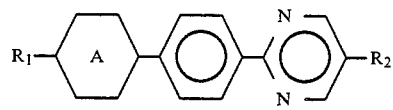

wherein $R_1$ and $R_2$ each represent an alkyl group or an alkyloxy group having 1 to 10 carbon atoms and

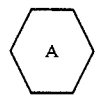

represents cyclohexane ring or benzene ring.

12 Claims, No Drawings

PYRIMIDINE DERIVATIVES

BACKGROUND OF THE INVENTION

1. Field of the Invention

This invention relates to novel organic compounds, and more particularly it relates to novel liquid crystal compounds useful as a component of liquid crystal materials.

2. Description of the Prior Art

As well known, liquid crystal substances not only have been applied to display elements using nematic liquid crystals having a twisted liquid crystal arrangement (the so-called TN cell), but also have been broadly applied to display elements utilizing a guest-host effect of liquid crystals or mixtures thereof containing a suitable pigment, and further, DS type display elements utilizing a dynamic scattering effect of liquid crystals, display elements utilizing a cholesteric-nematic phase transition of liquid crystals, DAP type display elements utilizing an electric field-controlling birefringence effect of liquid crystals, etc. At present, however, no single compound is existent which satisfies by itself these characteristics i.e. liquid crystal temperature range, actuation voltage, response properties, etc., and it is the present status that substances which are endurable to practical use to a certain extent have been obtained by mixing several kinds of liquid crystal compounds.

The object of the present invention is to provide compounds useful as a component constituting such superior, practical and stable liquid crystal compositions.

SUMMARY OF THE INVENTION

The present invention resides in:
5-substituted-2-(4'-substituted biphenylyl)pyrimidines and 5-substituted-2-[4'-(trans-4"-substituted cyclohexyl)phenyl]pyrimidines expressed by the general formula

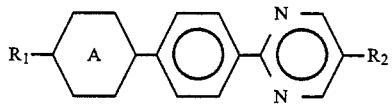 (I)

wherein $R_1$ and $R_2$ each represent an alkyl group or an alkyloxy group having 1 to 10 carbon atoms and

represents cyclohexane ring or benzene ring.

DESCRIPTION OF THE PREFERRED EMBODIMENTS

The compounds of the formula (I) of the present invention are liquid crystal compounds having a very large anisotropy of refractive index, a low viscosity for three-rings compounds, a comparatively broad liquid crystal temperature range and a superior stability.

The compounds of the present invention have a superior compatibility with other liquid crystal compounds; hence when they are mixed with compounds of liquid crystals of one to several kinds of groups such as biphenyl group, ester group, azoxy group, cyclohexanecarboxylic acid phenyl ester group, phenylcyclohexane group, phenylmetadioxane group, phenylpyrimidine group, etc., there can be exhibited effectiveness of improving various response characteristics, contrast and sharpness and also broadening their liquid crystal temperature ranges.

As for liquid crystal compounds having pyridine ring, those having two rings such as compounds expressed by the general formula

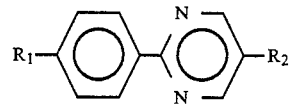

wherein $R_1$ and $R_2$ each represent alkyl, alkyloxy, acyl, cyano, etc., have so far been known (see DE No 2,257,588, Japanese patent publication No. 55-6632 (G.B. No. 1,473,990), Japanese patent application laid-open No. 55-157,571 (G.B. No. 2,049,692), Japanese patent application laid-open No. 56-53661 (U.S. Pat. No. 4,311,610), etc.). However, any of such compounds have narrower liquid crystal temperature ranges than those of the present invention. Further, as for liquid crystal compounds of pyrimidine group having three directly linked rings, compounds expressed by the general formulas

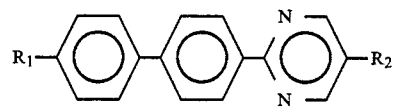

wherein one of $R_1$ and $R_2$ is CN and another is alkyl, alkyloxy, etc.,

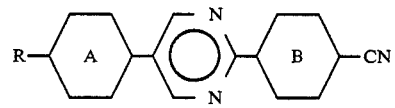

wherein

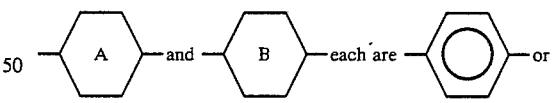

and R is alkyl, etc., and the like, have been known (Japanese patent publication No. 55-27056 (U.S. Pat. No. 4,062,798); Japanese patent application laid-open No. 55-104270 (G.B. No. 2,042,533, U.S. Pat. No. 4,273,929); Japanese patent application laid-open No. 57-95965 (G.B. No. 2,085,877).

However, these compounds necessarily contain CN group at one end of the molecules, in order to have a large Δε value; hence they have a smaller Δn value, a higher viscosity and a lower stability than those of the compounds of the present invention. Further the abovementioned No. 57-95965 discloses liquid crystal compounds of pyrimidine group having three directly linked rings such as those expressed by the general formula

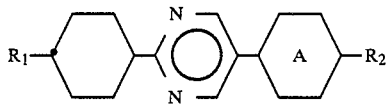

wherein $R_1$ and $R_2$ each represent alkyl, etc., and

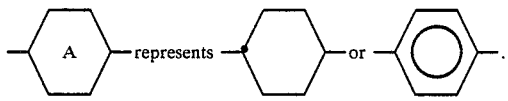

However, if pyrimidine ring is positioned at the center of the three rings, two phases i.e. a smectic phase and a nematic phase, constitute a liquid crystal phase, whereas the compounds of the present invention exhibit only a broad nematic phase; hence they are practically superior.

Next, the preparation of the compounds (I) of the present invention will be described in detail. First, its outline will be illustrated by way of the following equations:

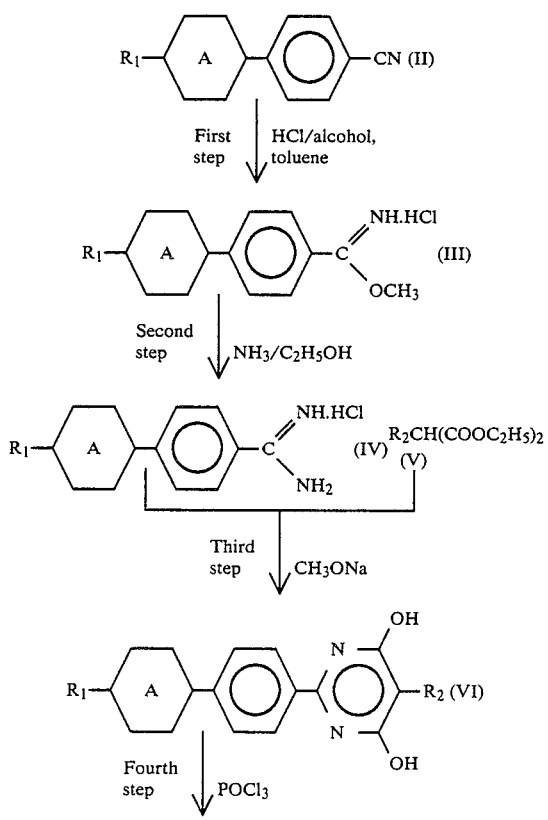

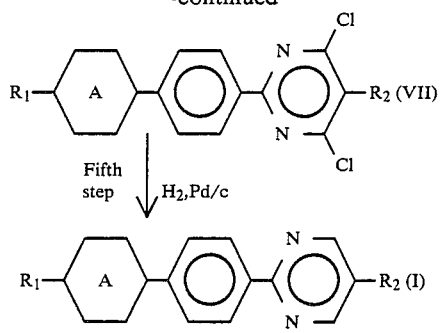

In the above equations, $R_1$ and $R_2$ each represent the same meanings as defined above.

First, a commercially available compound of the formula (II) having 4-substituted cyanophenyl group as a starting raw material is dissolved in an alcohol and toluene and reacted with HCl gas to obtain a compound of the formula (III) i.e. an imide ether hydrochloric acid salt derivative, which is then reacted with ethanol solution of $NH_3$ to obtain a compound of the formula (IV), i.e. an amidine hydrochloric acid salt derivative, which is then subjected together with a compound of the formula (V) i.e. an alkyl or alkyloxymalonic acid diethyl ester to a cyclization reaction in the presence of sodium methoxide, to obtain a compound of the formula (VI) i.e. a 2,5-substituted-4,6-dihydroxypyrimidine derivative, which is then chlorinated with phosphorus oxychloride to obtain a compound of the formula (VII) i.e. a 2,5-substituted-4,6-dichloropyrimidine derivative, which is then reduced with hydrogen in the presence of a paradium-carbon catalyst to obtain the objective compound (I).

The present invention will be described in detail by way of Examples.

EXAMPLE 1

Preparation of 5-hexyl-2-(4'-pentylbiphenylyl)-pyrimidine

First step

Commercially available 4'-pentyl-4-cyanobiphenyl (102.2 g, 0.410 mol) was dissolved in anhydrous methanol (27.9 g, 0.87 mol) and toluene (100 ml) and the solution was purged by nitrogen gas with stirring at $-5°$ C., followed by passing HCl gas (16.5 l) through the solution for 40 minutes and then agitating at $-5°$ C. for 6 hours.

The reaction mixture was allowed to stand at $-20°$ C. for 2 days to deposit crystals, followed by adding ethyl ether (30 ml), filtering and drying the crystals to obtain 4-(4'-pentylphenyl)phenylimide acid methyl ester hydrochloric acid salt (yield 104.5 g, 80%). M.P.: 231° C.

Second step

Ethanol (300 ml) was added to 4-(4'-pentylphenyl)-phenylimide acid methyl ester hydrochloric acid salt (104.5 g, 0.329 mol) obtained at the first step, followed by further adding $NH_3$-ethanol solution (15.9% by weight) (700 ml) with stirring, agitating the mixture at 30° C. for 5 hours, further allowing it to stand at room temperature for 2 hours, filtering, distilling off ethanol in the filtrate, filtering and drying deposited crystals to obtain 4-(4'-pentylphenyl)phenylamidine hydrochloric acid salt (yield: 86.2 g, 96.5%).

Third step

Metal Na (5.0 g, 0.217 mol) was added to anhydrous methanol (100 ml) to obtain sodium methoxide, to which were then added 4-(4-pentylphenyl)phenylamidine hydrochloric acid salt (20.0 g, 0.066 mol) obtained at the second step and n-hexylmalonic acid diethyl ester (16.2 g, 0.066 mol), under ice cooling and stirring, followed by refluxing with stirring for 8 hours, then ice cooling, adding 20% hydrochloric acid (150 ml), filtering precipitates, washing crystals with water and methanol and drying to obtain 5-hexyl-2-(4'-pentylbiphenylyl)-4,6-dihydroxypyrimidine (yield: 26.2 g, 95%).

Fourth step

To 5-hexyl-2-(4'-pentylbiphenyl)-4,6-dihydroxypyrimidine (26.2 g, 0.063 mol) obtained at the third step were added phosphorus oxychloride (150 ml) and N,N'-diethylaniline (25 ml), followed by refluxing for 30 hours, then distilling off excess phosphorus oxytrichloride, pouring the reaction mixture while hot into an ice-cooled 10% aqueous solution of NaOH (500 ml), extracting the reaction mixture with toluene (200 ml), washing the toluene layer with 20% hydrochloric acid and water, then distilling off toluene, recrystallizing from n-heptane (100 ml) and drying to obtain 5-hexyl-2-(4'-pentylbiphenylyl)4,6-dichloropyrimidine (yield: 20.5 g, 72%).

Fifth step

To 5-hexyl-2-(4'-pentylbiphenylyl)-4,6-dichloropyrimidine (20.5 g, 0.0453 mol) obtained at the fourth step were added magnesium oxide (15.0 g), palladium-carbon (5%) (3.0 g), ethanol (200 ml) and water (15 ml), followed by causing the mixture to absorb hydrogen gas at room temperature till it was saturated therewith, filtering the reaction material, washing the residue with toluene, subjecting the toluene layer and the filtrate to distilling off, dissolving the residue in toluene (200 ml), washing the solution with 20% hydrochloric acid and 10% aqueous solution of NaOH, further washing with water till the liquid became neutral, distilling off toluene, and recrystallizing the residue from n-heptane (200 ml) to obtain the objective 5-hexyl-2-(4'-pentylbiphenylyl)pyrimidine (yield: 11.5 g, 66%). This compound had a C-N point of 81° C., a N-I point of 164° C., a viscosity at 20° C. $\eta_{20}$ of 36 cp and a $\Delta n$ of 0.25. The values of elemental analysis accorded well with the theoretical values as follows:

| Element | Observed values | Theoretical values |
|---|---|---|
| C | 83.8% | 83.89% |
| N | 8.8% | 8.86% |
| H | 7.2% | 7.25% |

EXAMPLES 2~34

Other compounds of the formula (I) were prepared according to Example 1. Their values of physical properties are shown in Table 1 together with the results of Example 1.

TABLE 1

| Example No. | In formula (I) R$_1$ | A | R$_2$ | C—N point (°C.) | N—I point (°C.) | $\eta_{20}$ (cp) | $\Delta n$ | $\Delta\epsilon$ |
|---|---|---|---|---|---|---|---|---|
| 2 | C$_2$H$_5$ | ⬡ | C$_4$H$_9$ | 91 | 161 | 30 | 0.27 | 8.5 |
| 3 | " | " | C$_5$H$_{11}$ | 105 | 167 | 32 | 0.27 | 9.2 |
| 4 | " | " | C$_6$H$_{13}$ | 83 | 155 | 27 | 0.25 | 7.9 |
| 5 | C$_3$H$_7$ | " | C$_2$H$_5$ | 150 | 179 | 28 | 0.30 | 11.2 |
| 6 | " | " | C$_4$H$_9$ | 87 | 175 | 37 | 0.27 | 8.5 |
| 7 | " | " | C$_6$H$_{13}$ | 83 | 168 | 36 | 0.25 | 7.9 |
| 8 | C$_5$H$_{11}$ | " | C$_5$H$_{11}$ | 77 | 173 | 35 | 0.24 | — |
| 1 | " | " | C$_6$H$_{13}$ | 81 | 164 | 36 | 0.25 | — |
| 9 | " | " | C$_7$H$_{15}$ | 124 | 168 | 37 | 0.27 | — |
| 10 | C$_7$H$_{15}$ | " | C$_3$H$_7$ | 81 | 168 | 29 | 0.27 | 7.9 |
| 11 | " | " | C$_4$H$_9$ | 63 | 157 | 29 | 0.25 | 7.2 |
| 12 | " | " | C$_6$H$_{13}$ | 97 | 157 | 35 | 0.24 | 6.5 |
| 13 | C$_2$H$_5$ | ⬡H | C$_2$H$_5$ | 115 | 158 | 43 | 0.19 | 6.5 |
| 14 | " | " | C$_3$H$_7$ | 100 | 173 | 30 | 0.19 | 3.9 |
| 15 | " | " | C$_4$H$_9$ | 91 | 159 | 48 | 0.17 | 4.5 |
| 16 | " | " | C$_5$H$_{11}$ | 91 | 162 | 26 | 0.18 | 3.9 |
| 17 | C$_3$H$_7$ | " | C$_2$H$_5$ | 109 | 184 | 27 | 0.21 | 6.5 |
| 18 | " | " | C$_3$H$_7$ | 97 | 198 | 32 | 0.20 | 5.9 |
| 19 | " | " | C$_4$H$_9$ | 79 | 179 | 36 | 0.21 | 3.9 |
| 20 | " | " | C$_5$H$_{11}$ | 92 | 184 | 39 | 0.19 | 5.2 |
| 21 | " | " | C$_6$H$_{13}$ | 95 | 170 | 41 | 0.15 | 6.2 |
| 22 | " | " | C$_7$H$_{15}$ | 106 | 169 | — | — | — |
| 23 | C$_4$H$_9$ | " | C$_2$H$_5$ | 106 | 174 | 46 | 0.20 | 5.9 |
| 24 | " | " | C$_3$H$_7$ | 80 | 187 | 38 | 0.19 | 5.2 |
| 25 | " | " | C$_4$H$_9$ | 83 | 172 | 38 | 0.17 | 5.2 |
| 26 | " | " | C$_5$H$_{11}$ | 63 | 173 | 30 | 0.16 | 3.9 |
| 27 | C$_5$H$_{11}$ | " | C$_2$H$_5$ | 116 | 178 | 33 | 0.18 | 6.5 |
| 28 | " | " | C$_3$H$_7$ | 101 | 187 | 38 | 0.19 | 5.2 |
| 29 | " | " | C$_4$H$_9$ | 79 | 175 | 33 | 0.19 | 4.5 |
| 30 | " | " | C$_5$H$_{11}$ | 73 | 177 | 44 | 0.19 | 3.9 |
| 31 | C$_3$H$_7$O | ⬡ | C$_2$H$_5$ | 146 | 205 | 56 | 0.32 | — |
| 32 | " | " | C$_5$H$_{11}$ | 132 | 204 | — | — | — |
| 33 | " | " | C$_6$H$_{13}$ | 123 | 189 | 54 | 0.27 | — |
| 34 | " | " | C$_7$H$_{15}$ | 101 | 191 | 47 | 0.25 | 12.2 |

EXAMPLE 35

(Use example 1)

A liquid crystal composition A consisting of

C$_3$H$_7$—⬡H—⬯—CN  30 parts by weight

C$_5$H$_{11}$—⬡H—⬯—CN  40 parts by weight

C$_7$H$_{15}$—⬡H—⬯—CN  30 parts by weight had a N-I point of 52.4° C., a viscosity at 20° C. $\eta_{20}$ of 23.1 cp and a dielectric anisotropy $\Delta\epsilon$ of 11.2 ($\epsilon_\parallel = 16.1$, $\epsilon_\perp = 4.9$). Further, when this composition was sealed in a TN cell of 10 μm thick, the resulting threshold voltage, saturation voltage and refractive index anisotropy Δn were 1.5 V, 2.0 V and 0.120 (ne=1.612, no=1.492), respectively.

When 5-heptyl-2-(4'-pentylbiphenyl)pyrimidine of Example 9 of the present invention (10 parts by weight) was added to the liquid crystal composition A (90 parts by weight), the resulting liquid crystal composition had a N-I point raised up to 61.5° C., a $\eta_{20}$ slightly raised up to 24.5 cp, a Δε of 11.0 ($\epsilon_{\parallel}$ =15.6, $\epsilon_{\perp}$=4.6), a threshold voltage of 1.6 V, a saturation voltage of 2.1 V and a Δn raised up to 0.135 (ne=1.629, no=1.494).

EXAMPLE 36

(Use example 2)

5-Ethyl-2-(4'-(trans-4''-propylcyclohexyl)phenyl)-pyrimidine (10 parts by weight) of Example 17 of the present invention was added to the same liquid crystal composition A (90 parts by weight) as used in Example 35. The resulting liquid crystal composition had a N-I point raised up to 63.1° C., a $\eta_{20}$ of 24.4 cp similar to that of the composition A, a Δε of 11.1 ($\epsilon_{\parallel}$ =15.7, $\epsilon_{\perp}$=4.6), a threshold voltage of 1.5 V, a saturation voltage of 2.1 V and a Δn raised up to 0.130 (ne=1.624, no=1.494).

COMPARATIVE EXAMPLE

which is a representative compound among high temperature liquid crystals having a large Δn value, currently used was added to the liquid crystal composition A (90 parts by weight) used in Examples 35 and 36. The resulting liquid crystal composition had a N-I point raised up to 66.7° C., a Δn raised up to 0.146 and also a $\eta_{20}$ much raised up to 27.5 cp.

Further, when the above mixing proportion was changed to 96.5 parts by weight of the liquid crystal composition A and 3.5 parts by weight of the above high temperature liquid crystal compound, the resulting liquid crystal composition had a $\eta_{20}$ of 24.5 cp, but its N-I point and Δn were reduced down to 57.6° C. and 0.129, respectively.

What we claim is:

1. A compound having the general formula

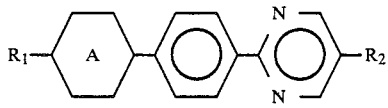

wherein $R_1$ and $R_2$ each represent an alkyl group or an alkyloxy group having 1 to 10 carbon atoms and

represents a cyclohexane ring or benzene ring.

2. A compound according to claim 1 which is a 5-substituted-2-(4'-substituted biphenylyl)-pyrimidine.

3. A compound according to claim 1 which is a 5-substituted-2-[4'-(trans-4''-substituted cyclohexyl)phenyl]-pyrimidine.

4. A compound according to claim 1 which is a 5-alkyl-2-[4'-(trans-4''-alkylcyclohexyl)phenyl]-pyrimidine expressed by the general formula

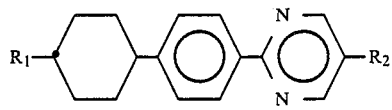

wherein $R_1$ and $R_2$ each represent an alkyl group having 1 to 10 carbon atoms.

5. A compound according to claim 4 wherein $R_1$ and $R_2$ each have 2 to 7 carbon atoms.

6. A liquid crystal composition which contains at least two liquid crystal components wherein at least one component thereof is a compound as set forth in claim 1.

7. A liquid crystal composition which contains at least two liquid crystal components wherein at least one component thereof is a compound as set forth in claim 2.

8. A liquid crystal composition which contains at least two liquid crystal components wherein at least one component thereof is a compound as set forth in claim 3.

9. A liquid crystal composition which contains at least two liquid crystal components wherein at least one component thereof is a compound as set forth in claim 4.

10. A liquid crystal composition which contains at least two liquid crystal components wherein at least one component thereof is a compound as set forth in claim 5.

11. As a compound according to claim 1, 5-hexyl-2-(4'-pentylbiphenylyl)-pyrimidine.

12. As a compound according to claim 1, 5-ethyl-2-(4'-trans-4''-propylcyclohexyl phenyl)-pyrimidine.

* * * * *